United States Patent
Suh et al.

(10) Patent No.: US 8,026,297 B2
(45) Date of Patent: Sep. 27, 2011

(54) DENTAL PRIMER ADHESIVE SYSTEM AND OPTIONAL HYDROPHOBIC RESIN

(75) Inventors: Byoung Suh, Oak Brook, IL (US); Rui Yin, Buffalo Grove, IL (US); Michelle Schiltz-Taing, Carpentersville, IL (US); Adriana Pigozzo Manso, South Barrington, IL (US)

(73) Assignee: Bisco, Inc., Schaumburg, IL (US)

( * ) Notice: Subject to any disclaimer, the term of this patent is extended or adjusted under 35 U.S.C. 154(b) by 476 days.

(21) Appl. No.: 12/021,808

(22) Filed: Jan. 29, 2008

(65) Prior Publication Data

US 2008/0182921 A1 Jul. 31, 2008

Related U.S. Application Data

(60) Provisional application No. 60/898,014, filed on Jan. 29, 2007.

(51) Int. Cl.
*A61K 6/083* (2006.01)
*A61C 5/00* (2006.01)

(52) U.S. Cl. .................. 523/118; 433/228.1; 106/35

(58) Field of Classification Search .............. 523/118; 433/228.1
See application file for complete search history.

(56) References Cited

U.S. PATENT DOCUMENTS

| | | | | |
|---|---|---|---|---|
| 5,425,641 | A | * | 6/1995 | Fischer .......................... 433/226 |
| 5,525,647 | A | * | 6/1996 | Eichmiller .................... 523/105 |
| 5,749,733 | A | * | 5/1998 | Qian et al. ................. 433/228.1 |

* cited by examiner

*Primary Examiner* — Tae H Yoon
(74) *Attorney, Agent, or Firm* — Ice Miller LLP

(57) ABSTRACT

The present application relates to a polymerizable dental primer/adhesive system comprising a primer component having a relatively hydrophilic monomer component in an amount that renders the system relatively hydrophilic before polymerization of the system and capable of penetrating a prepared dental surface such as etched tooth dentin or enamel, and a multi-functional cross-linking agent in an amount that renders the system relatively hydrophobic after polymerization. A polymerizable hydrophobic monomer component is also included in the primer. The inclusion of said hydrophobic polymerizable monomer and said multi-functional cross-linking agent improves the long term stability or durability of the polymerized primer system to the dental restoration and to the tooth, dentin, enamel and other dental surfaces. An additional hydrophobic resin can also be employed with the primer adhesive system. The dental primer adhesive system exhibits greater stability and durability over time when compared to other dental adhesive systems.

14 Claims, No Drawings

DENTAL PRIMER ADHESIVE SYSTEM AND OPTIONAL HYDROPHOBIC RESIN

PRIORITY

The present application claims priority to U.S. Provisional Patent Application Ser. No. 60/898,014, filed Jan. 29, 2007, which is incorporated by reference herein.

DESCRIPTION OF RELATED TECHNOLOGY

Advances in dental restorative techniques include the use of various materials such as composite resins to effect tooth filling or other restorative processes. Other advances include the use of dental components such as thin wire braces and other types of dental components made of metal, ceramics, resins or other bio-compatible substances. Depending on the clinical application, such restoratives and components may be applied directly to the tooth dentin and/or enamel, or may be applied to other bio-compatible substrates such as metals, ceramics, resins, amalgams, or other restorative materials which may already exist in the patient and/or are to be added as part of the clinical treatment.

Common to the foregoing materials and techniques is the need for bonding systems to enhance the bonding of the restorative or other dental component to the chosen dental substrate. Ideally, such enhancement would provide bond strengths which approach the strength of the underlying substrates. In addition, ideal bonding systems would also be simple for the dental professional to use in a manner which requires a minimum of time for the patient in the chair.

Several bonding systems and techniques have been reported in the literature which have achieved some, but not all of the above-stated goals. Such bonding systems can be divided into three general categories, multiple-component primer systems, two component primer systems, and single-component primer systems.

A. Multiple Component Bonding Systems

A general discussion of multiple-component bonding systems and their predecessors is set out in Suh, "All-Bond—Fourth Generation Dentin Bonding System," J. Esthetic Dentistry, Vol. 3, No. 4, pp. 139-147 (July-August, 1991) and in Bowen U.S. Pat. No. 5,270,351 at Col. 1, lines 29-Col. 2, line 36 and Col. 2, lines 54-64, the disclosures of which are hereby incorporated by reference. Briefly summarized, the early generation bonding systems generally disclosed at Col. 1 and 2 of the '351 patent began with simple pretreatment of the dental substrate with mordants and/or acidic solutions before application of the dental restorative or component. Such systems, while simple to use, did not provide high bond strengths on substrates such as tooth dentin.

Those low bond strengths led to the development of the multiple-component bonding systems discussed at Col. 2 of the '351 patent and discussed in detail in the J. Esthetic Dentistry article at pp. 139-147. Such systems generally employed the older generation system's first step of pretreatment of tooth dentin or enamel with acidic solutions to decalcify and remove dentin smear layer and to etch tooth enamel (a technique often referred to as "total etch" process, as both dentin and enamel may be etched using a low pH solution). The multi-component systems then employed two or more separate "primer" or "adhesive enhancing" compounds to further enhance bonding between the substrate and the dental restorative. However, the primers in such systems must either (1) be applied separately and sequentially to the dental substrate, or (2) must be mixed together by the dental professional in the office immediately before use on the patient to prevent premature polymerization of the components.

The first type of such multiple-component primer systems is exemplified in Bowen U.S. Pat. Nos. 4,514,527, 4,551,550, 4,558,756 and 4,659,751, and U.S. Pat. No. 4,964,911 Ivson et al., (and related Ibsen et al. U.S. Pat. re 34937) discussed at Col. 2 of the '351 patent. Those earlier patents disclose, inter alia, two or three component primer systems employing the separate steps of treating the dental substrate with (1) an acidic acid solution of inorganic acids, polycarboxylic acids and metal salts of such acids capable of changing valence states, (2) applying a first primer compound comprising N-arylglycine and derivatives such as NTG-GMA (the adduct of N(p-tolyl)glycine and glycidyl methacrylate), NPG (N-phenylglycine), and other amino acids and metal salts thereof to the substrate, followed by (3) applying a second polymerizable adhesive bonding monomer to the substrate comprising PMDM, BDTA-HEMA, 4-META, or other polymerizable acidic monomers disclosed therein and having groups or moieties that do not interfere with polymerization. Although some of those systems report achieving moderate bond strengths for bonding to substrates such as tooth dentin, from about 1600 to about 2500 p.s.i (11-17 Mega Pascals (1 MPa=145 psi.)), such multi-component/multi-step methods are necessarily complicated for the dental professional and time-consuming for the patient.

B. Two-Component Primer Systems

As an alternative to multiple-component primer systems, Bowen and others, including applicant's assignee, Bisco, Inc., have reported development of two-component primer systems. See e.g., Bowen U.S. Pat. Nos. 5,320,886 and 5,270,351, Suh et al. article cited above and U.S. Pat. No. 5,348,988 and Bunker U.S. Pat. No. 4,544,467. Such systems involve steps whereby the dental professional admixes the two primer components immediately prior to application of the mixture to the dental substrate. Immediate application is required in such systems because the primer composition begins to polymerize upon mixing due to the chemical nature of the primer molecules, at least one of which contains ethylenically unsaturated (vinyl) groups whose polymerization is initiated by the tertiary amine group present on the other primer component of the system. The two-component primer bonding systems typically require an acid-etch step to provide a secure bond between the dentin and/or enamel and the primer, resulting in the so-called "hybrid layer" wherein the dentin/enamel and primer interface with one another.

A different type of a two-component primer bonding system is disclosed in Waknine U.S. Pat. No. 5,276,068. That two-component system comprises a polymerization initiator and a polymerizable compound which are packaged separately. The first step in that system requires application of polymerization initiator alone to the dental substrate. In a second step, the polymerizable compound is applied to the substrate. Polymerization begins when the polymerizable compound comes into contact with the initiator on the substrate surface.

Some of the aforesaid multiple-component primer systems were reported as providing only moderate dentin adhesive bonding strengths. For example, the data included in the Bowen '351 and '886 patents show dentin adhesive bond strengths of from about 10 to about 15 MPa. Moreover, the higher bond strengths reported in the '351 patent were achieved only after an additional step and component, comprising applying an unfilled adhesive resin monomer to the primed substrate before application of the dental restorative composite material, was added to the restorative process. (See '351 patent, Example 1.) The Waknine '068 patent also reports relatively low bond strengths in the 10 MPa range and also used an additional step of application of a commercial bonding resin (see Examples 22-23.) Bunker et al. reported slightly lower dentin shear bond strengths of between about 5 MPa and 8 MPa (49.3 to 86.5 kg/cm$^2$).

Surprisingly, Suh et al.'s two-component primer system utilizing polymerizable acidic monomer biphenyl dimethacrylate (BPDM) achieved bond strengths of between 22 and 27 MPa for dentin bonding, which approaches or equals the point of cohesive failure of tooth dentin. High bond strengths of around 23-26 MPa were also achieved with that two component priming system for bonding to tooth enamel. (See, e.g., J. Esthetic Dentistry article, Hydrophilic Primer Adhesive System and Optional Hydrophobic Resin).

C. Single Component Primer Systems

Additionally, there have been reported certain "one-component" or "single step" dental bonding systems. See, for example, Blackwell et al. U.S. Pat. Nos. 4,657,941 and 4,816,495 and Huang et al. U.S. Pat. No. 4,966,934 all of which are assigned to Dentsply Research and Development Corporation (hereinafter also collectively referred to as the Dentsply patents) and Bunker U.S. Pat. No. 5,304,585.

The Bunker et al. system is reported as involving polymerizable phosphoric acid ester adhesives. Such compositions are generally disclosed therein as capable of being packaged with polymerization initiators in the presence of polymerization inhibitors and other compounds in one package. (See '585 patent, col. 10, line 31 to col. 11, line 8.) However, such one-component packaging is not exemplified in the '585 patent. Instead, a two-component was tested in Example 1 of that patent, involving admixing of the polymerization initiator sodium benzenesulfonate first component with the phosphorous ester monomer second component immediately before application to the tooth substrate. Bunker et al. also reported relatively low bond strength to dentin of around 9 MPa. (See '585 patent, col. 12, lines 16-42.)

The Dentsply patents also disclose alleged one-component dentin and enamel bonding primer and adhesive systems. Such systems are reported as based inter alia on phosphorous-containing adhesion promoter compounds. However, the phosphorous-based bonding systems disclosed in the examples of '941 and '495 patents all gave relatively low bond strengths of 8.39 MPa or less.

The dipentaerythritol pentaacrylate phosphoric acid ester-based (PENTA) bonding systems disclosed in the '934 patent were reported as generating higher dentin bond strengths in the range of 10-27 MPa. (See '934 patent Example 10.) However, also reported therein is data showing that the higher reported bond strength systems were not stable over time, with the 27 MPa strength system reported as decreasing to around 10 MPa or less after 1-2 weeks storage of the system at elevated temperatures. (See '934 patent, Table VIII.) Moreover, the higher bond strengths reported in the '934 patent were in actuality two-component systems in which a second commercial, unfilled adhesive bonding resin component was used after application of the phosphorous primer composition. (See Example 4 and Example 10 at Col. 17, line 60-Col. 18, line 53 and Tables IX and X.) The "most promising" PENTA-based bonding systems disclosed in the '934 patent were further tested with that additional second adhesive component and step which were reported to provide bonding strengths from about 17 to 20 MPa. (See Table X.) In all three Dentsply patents, the primer curing system was reported as light-curing done after either application of the composite resin material and/or after application of a separate adhesive resin. (See Example 4 of '941, 495 and 934 patents.)

U.S. Pat. No. 4,525,256 discloses certain one component photopolymerizable resins containing certain tertiary amine accelerators. However, such compositions are composite (filled) resins, and not dental primer or adhesive compositions. (See '256 patent, Examples 1-3.)

U.S. Pat. No. 5,295,824 discloses inter alia plastic orthodontic devices with a "shelf-stable" monomeric adhesive layer pre-coated and "solvated" into the plastic device. The bond strengths reported therein are about 10-20 kg, which if meant to be kg/cm$^2$, translate to rather low levels of around 2-4 MPa.

PCT application publication No. WO/93/02630 discloses an adhesive-coated orthodontic bracket. The bracket's adhesive layer comprises ethoxylated diglycidyimethacrylate of Bisphenol A (Bis-GMA), Bis-GMA and/or other monomers and photo-initiator catalysts and inhibitors. The bond strength of such pre-coated brackets were reported to be in the range of 54-104 kg/cm$^2$ (about 5-10 MPa).

D. Bond Strength and Etching Systems

In general, the three step process of etching/rinsing, applying a primer(s), followed by an adhesive, and thereafter followed by a restorative resin has been reported in the literature as the "gold standard" of achieving high bond stability and durability in a dental restoration bonded to dentin. De Munck et al., J. Dent. Res. 84(2):118-124 (2005). However, three step process restorations are reported to be more labor intensive and technique sensitive, and the technique used can significantly influence the resultant bond strength. Id. Nonetheless, reported laboratory results show that three step etch and rinse systems provide in an average initial dentin microtensile bond strength (μTBS) that is higher than that reported for acid etched and self-etched two-step adhesive systems. Id. Self-etched single component systems were reported to have the lowest initial microtensile bond strengths. Id.

Commercially available single-component self-etching bonding systems are reported as being promoted for use primarily for ease of use and low technique sensitivity, as well as good performance in class V clinical trials. Inoue et al.; J. Dent. Res 84(12):1160-1164 (2005). However, aside from the relatively low initial dentin and enamel bond strength, self-etch single-component systems employing functional acidic methacrylate monomers with water that are stored together in a single bottle have been reported to degrade via hydrolysis during storage. Nishiyama et al., J. Dent. Res. 85(5):422-426 (2006) (describing such simplified self-etch adhesives as having "poor shelf lives"). Further, such degradation has been reported to occur as early as one month from the date of manufacture when kept at 25° C. Id.

E. Bond Strength and Hydrophilicity

Apart from initial bond strength, recent studies have tested the bond strength of various resins when exposed to conditions approximating those experienced in vivo over time. In particular, it has been reported that resins formed from relatively hydrophilic monomers results in a substantially weaker bond strength after cured, largely due to hydrolysis, elution, and the formation of water trees within the hybrid layer. Yiu C K, Biomaterials (25):5789-5796 (2004). Those, studies report that the greatest absorption of water in hydrophilic compounds occurs within the first day of exposure to water. Id. In addition, hydrophilic acidic resins were reported to show the greatest decrease in bonding strength within the first month of exposure to water. Id. Recent studies suggest that some commercial single-step dental bonding systems are hydrophilic and have their greatest water-absorption during the first few weeks of storage in water. Malacarne J, Dent. Mater. (22): 973-980 (2006).

Therefore, an improved two or three-step restoration system showing higher initial bond strength and improved bond stability and durability over time would be appreciated by those in the art.

DESCRIPTION

According to the present invention, an improved dental adhesive and restoration system is disclosed. In particular, it has been found that use of a primer A and B system having a polymerizable component that comprises a monomer component relatively hydrophilic before polymerization of the system and is relatively hydrophobic after polymerization of the system, when used alone or in association with an additional hydrophobic resin, creates strong initial bonding with improved long term stability and durability.

More specifically, it has been found that inclusion in one of the primer components of a relatively high cross-linking agent such as a multifunctional (meth)acrylate monomer having at least four functional groups improves the stability of the system relative to degradation due to exposure of the system to water. In addition, the inclusion in a primer component of a relatively hydrophobic monomer(s) improves the stability of the system.

In particular, it has been found that when a primer/adhesive system comprising a first primer component A comprising ethanol and an amino acid salt derivative N(p-tolyl)glycine glycidyl methacrylate magnesium salt (Mg NTG-GMA) and a second primer component B comprising polymerizable acidic monomer BPDM (biphenyl dimethacrylate), dipentaerythritol pentaacrylate ("DPEPA"), relatively hydrophobic resin BisGMA or ethoxylated BisGMA, and initially hydrophilic monomer 2-hydroxyethyl-methacrylate (HEMA), and camphorquinone ("CQ") creates an effective hybridization layer when mixed and applied to a tooth surface prepared with an acid etch (of approximately 20%-50% phosphoric acid) and rinsed with water prior to application of the primer mix.

In one embodiment, a hydrophobic dentin/enamel resin is applied over a tooth surface prepared and primed with the primer/adhesive system described above. For example, a hydrophobic resin may comprise BisGMA, urethane dimethacrylate ("UDMA"), triethyleneglycol dimethacrylate ("Tri-EDMA"), ethyl 4-dimethylaminobenzoate ("EDMAB"), CQ, and 4-methoxyphenol ("MEHQ").

It has also been found that removal of monomers such as HEMA from the resin, while including such a hydrophilic monomer in the primer, results in a high initial bond strength with improved long term bond strength.

EXAMPLE I

For example, according to one exemplary embodiment, a primer/adhesive system comprises a part A comprising from approximately 90-99% (by weight) ethanol and approximately 1%-10% (by weight) of an amino acid or its salt derivative such as Mg NTG-GMA; and a part B comprising a polymerizable acidic monomer such as BPDM at about 5%-30% (by weight), about 10%-40% HEMA (by weight), about 5%-15% DPEPA (by weight), about 20%-60% (by weight) of relatively hydrophobic resin BisGMA or ethoxylated BisGMA, and about 0.1%-1% CQ (by weight). According to one exemplary embodiment, Part B may comprise a polymerizable acidic monomer such as BPDM in an amount about 10% (by weight), about 38% HEMA (by weight), about 10% DPEPA (by weight), about 41% (by weight) of relatively hydrophobic resin BisGMA or ethoxylated BisGMA, about 0.5% CQ (by weight), and about 0.5% EDMAB (by weight). Additionally, a hydrophobic resin may comprise approximately 20-30% BisGMA (by weight), approximately 20-30% UDMA (by weight), approximately 30-47.77% TriEDMA (by weight), approximately 1.00-1.75% EDMAB (by weight), approximately 0.30-0.45% camphorquinone (by weight), and approximately less than 0.1% MEHQ (by weight). As shown below in Table 1, the initial bond strength to dentin when a first acid etch/rinse is applied is approximately 60 MPa, with no statistically significant reduction in strength after 24 hours. In this instance, microtensile bond strength was tested according to the methods generally described in Sano et al., Dent Mater (10): 236-240 (1994). Optionally, the resin may contain a filler or radiopaque filler such as Ytterbium fluoride (YbF3) that may comprise approximately 10%-50% by weight of the resin composition.

When the primer is used along with the HEMA free resin, the bond strength after 24 hours did not decrease.

TABLE 1

MICROTENSILE BOND STRENGTH TO DENTIN

| | Example I Primer (A + B Only) | | Example 1 Primer (A + B) & Resin) | |
|---|---|---|---|---|
| | Strength | Standard Deviation ("SD") | Strength | Standard Deviation ("SD") |
| Same Day 37° C. in H$_2$O LC | 60.0 MPa | 14.7 MPa | 55.3 MPa | 9.8 MPa |
| 24 Hours at 37° C. in H$_2$O LC | 60.0 MPa | 13.2 MPa | 62.4 MPa | 11.1 MPa |
| Self Cure 24 Hours at 37° C. in H$_2$O | 58.2 MPa | 9.3 MPa | NA | NA |

Further, according to one embodiment of the present application, long term testing over 24 months, as shown in Table 2 below, shows that the above-described primer composition alone continues to retain microtensile bond strength ("μ-TBS") over the entire period when exposed to water in an accelerated aging test when used alone or with a filled Dentin Enamel ("D/E") resin.

TABLE 2

ACCELERATED AGING TEST OF BOND TO DENTIN
ULTRADENT SHEAR BOND TEST

| | Prior Art Primer with D/E Resin | | Example 1 Primer (A + B) Only | | Example 1 Primer (A + B) & Filled D/E Resin | |
|---|---|---|---|---|---|---|
| Light Cure | Strength | Standard Deviation | Strength | Standard Deviation | Strength | Standard Deviation |
| Initial 24 Hrs at 37° C. in H$_2$0 | 33.8 MPa | 5.9 MPa | 35.1 MPa | 4.6 MPa | 41.6 MPa | 6.6 MPa |
| 24 Months at 37° C. in H$_2$0 | 23.5 MPa | 7.0 MPa | 34.4 MPa | 4.6 MPa | 47.9 MPa | 6.8 MPa |

In addition, the sample was tested according to the use of the Ultradent shear bond test by using an Ultradent jig as described generally in the article: Pashley et al., Dent. Mater. 11: 117-125 (1995). Further testing in water for 24 months and 45 months at 37° C. further supports the findings set forth in Table 2 above. As summarized below in Table 3, aging testing in water showed that shear bond strength did not appreciably reduce over 24 months in the novel primer/adhesive system described as Example 1. Further, only slight reduction in shear strength was shown in the water aging test at 45 months.

Aging testing of the primer disclosed above when further bonded with a filled D/E resin as discussed above further showed surprising results compared to the teachings of Yiu et al. Specifically, when tested in water for 24 months and 45 months at 37° C., the bonding strengths of the primer/adhesive system to dentin when used along with a hydrophilic resin such as that described above show that the system remained stable, exhibiting resistance to water-induced degradation.

TABLE 3

LONG TERM AGING TEST IN $H_2O$ - SHEAR BOND STRENGTH OF BOND TO DENTIN AS SUBSTRATE ULTRADENT SHEAR BOND TEST (MPa)

| Light Cured | Example 1 Primer (A + B) Only | | Example 1 Primer (A + B) & Filled D/E Resin | |
|---|---|---|---|---|
| | Strength | Standard Deviation | Strength | Standard Deviation |
| Initial at 37° C. in $H_2O$ LC | 35.1 | 4.6 | 41.6 | 6.6 |
| 24 Months at 37° C. in $H_2O$ LC | 34.4 | 4.6 | 47.9 | 6.8 |
| 45 Months at 37° C. in $H_2O$ LC | 29.6 | 6.4 | 45.9 | 6.1 |

Table 4 shows the bond strength of adhesives commercially available when compared to a primer/adhesive system according to the present invention. Each of the commercially available bonding systems were compared with the primer/adhesive system as disclosed above, as well as the primer/adhesive system and an additional hydrophobic resin comprising 29.5% BisGMA (wt), about 29.5% UDMA (wt), about 39% TriEDMA (wt), about 1.435% EDMAB (wt), and about 0.369% CQ (wt), and 0.025% MEHQ, each of which were applied using the total etch technique. As will be appreciated, the primer/adhesive system according to the present invention, when used alone or in combination with a hydrophobic resin, resulted in an initial bond that is very high, coupled with long term bond stability and durability that is better than any other adhesive system tested.

TABLE 4

LONG TERM AGING TEST OF ADHESIVES µ-TBS - EXPOSED SPECIMENS WITH DENTIN AS A SUBSTRATE (ALL RESULTS IN MPa)

| Total Etch Adhesives | 24 HR (SD) | 6 Weeks (SD) | 24 Weeks (SD) |
|---|---|---|---|
| Example 1 Primer (A + B) Only at 37° C. in $H_2O$ LC | 57.7 (15.8) | 65.7 (11.8) | 65.2 (15.6) |
| Example 1 Primer (A + B)+ Filled Hydrophobic Resin at 37° C. in $H_2O$ LC | 62.8 (4.9) | 61.4 (13.6) | 61.0 (10.1) |
| Scotchbond MP at 37° C. in $H_2O$ LC | 49.1 (14.0) | 64.0 (11.7) | 44.1 (15.3) |
| One-Step at 37° C. in $H_2O$ LC | 65.2 (11.3) | 69.5 (14.2) | 58.0 (13.4) |
| Singlebond at 37° C. in $H_2O$ LC | 75.1 (12.4) | 66.6 (12.6) | 54.0 (23.0) |

Further, according to at least one embodiment of the present application, long term testing over 6 months, as shown in Table 5 below, shows that one exemplary embodiment of the adhesive system, when bonded to dentin continues to retain microtensile bond strength ("µ-TBS") over the entire period when exposed to water at 37° C. in an aging test. According to at least one embodiment, a dental adhesive system comprising a Part A primer component comprising 2% Mg-NTG-GMA (wt) and 98% absolute ethanol (wt), and a relatively hydrophilic Part B primer component comprising 10% BPDM (wt), about 38.75% HEMA (wt), about 10% DPEPA (wt), about 41% BisGMA (wt), about 0.25% CQ (wt); and a relatively hydrophobic liner comprising about 29.5% BisGMA (wt), about 29.5% UDMA (wt), about 39% TriEDMA (wt), about 1.435% EDMAB (wt), and about 0.369 CQ (wt), and 0.025 MEHQ (the "Sample").

TABLE 5

LONG TERM AGING TEST OF ADHESIVES µ-TBS - EXPOSED SPECIMENS WITH DENTIN AS A SUBSTRATE (ALL RESULTS IN MPa)

| Total Etch Adhesives | 24 HR (SD) | 3 months | 6 Months |
|---|---|---|---|
| Sample in water | 42.22 (13.53) | 46.25 (13.32) | 52.52 (14.29) |
| Sample + hydrophobic resin in water | 48.41 (7.53) | 47.65 (6.46) | 46.62 (9.82) |

In yet another embodiment, a dental adhesive system according to at least one of the above formulations further comprises the use of chlorhexidine dissolved in ethanol or a comparable alcohol or other solvent having a solubility coefficient approximately similar thereto as a wetting solution prior to etching the prepared dentin surface. As it is known that chlorhexidine is a matrix metalloproteinase ("MMP") inhibitor, and studies have indicated that endogenous MMP's may contribute to collagen degradation and weakening adhesive bond strength, the below Table 6 shows the results of testing used to determine whether use of chlorhexidine interferes with a dental adhesive system according to at least one of the above formulations.

Four solutions were prepared: a control solution of water; a 1% chlorhexidine diacetate in water solution (CHX/Water); ethanol only (Ethanol); and 1% chlorhexidine diacetate in ethanol (CHX/Ethanol). Flat dentin surfaces were etched with 32% phosphoric acid, Uni-etch BAC (Bisco Inc.) during 15 s, rinsed thoroughly with water (30 s), and dried with absorbent paper. Any visible water was remaining on the dentin surface was removed and surfaces were re-wetted during 30 seconds with one of the solutions prepared, including the control groups (water and ethanol without chlorhexidine). The excess of the solution was removed with tissue-paper and an adhesive according to one of the embodiments discussed above (Sample components A and B of Table 5 above), was applied with smooth and continuous rubbing during 15 seconds and left undisturbed for 15 seconds. A gentle air stream was applied to evaporate the solvents, and subsequently it was light-cured for 20 s (500 mW/cm 2). Four-mm resin build-ups were constructed incrementally, using Aelite All-purpose Body (Bisco). After storage in water at 37° C. for 24 h, teeth were cut into beams for microtensile test (0.5 mm/min). Half of the beams were tested immediately (24 h) and the other half was stored in distilled water, which was changed every month for 6 months. When the storage period was completed, the remaining beams were tested. Data were analyzed by two-way ANOVA and Tukey for pairwise comparisons ($\alpha=0.05$) to evaluate effects of treatments and testing periods. The tests below show that there were no significant negative effects of treating the dentin with any of the chlorhexidine solutions prior to bonding, either in initial bond strength or at the 6 month period. It is believed that long term bond strength may be improved due to the MMP inhibitive effects of chlorhexidine, as well as the anti-microbial effects of chlorhexidine. Further, according to another embodiment, chlorhexidine dissolved in ethanol is utilized as a portion of Part A or Part B of the adhesive systems disclosed above.

TABLE 6

BOND STRENGTH AS A FUNCTION OF STORAGE TIME
OF ADHESIVES μ-TBS - CHLORHEXIDINE ("CHX")
INFUSED SAMPLES WITH DENTIN AS A SUBSTRATE
(ALL RESULTS IN MPa)

| Solution Used to Treat Prepared Dentin | 24 HOURS | 6 MONTHS |
| --- | --- | --- |
| WATER | 49.41 ± 10.75 (19) | 58.68 ± 8.95 (23) |
| CHX + WATER | 51.27 ± 17.28 (16) | 55.13 ± 15.87 (16) |
| ETHANOL | 58.27 ± 10.42 (20) | 57.31 ± 10.11 (21) |
| CHX + ETHANOL | 53.08 ± 15.80 (21) | 59.71 ± 12.92 (19) |

What is claimed is:

1. A dental adhesive system comprising:
  a. a first portion and a second portion operable to be mixed prior to application to a dental surface, wherein
    (i) the first portion comprises ethanol and N(p-tolyl) glycine glycidyl methacrylate magnesium salt;
    (ii) the second portion comprises biphenyl dimethacrylate (BPDM), 2-hydroxyethyl-methacrylate (HEMA), Bis-phenol glycidlymethacrylate (BisGMA), a multifunctional cross-linking agent and a light cure initiator system; and
    (iii) wherein the resultant adhesive system comprises a hybrid layer when applied to dentin that has been treated with an acidic solution.

2. The dental adhesive system of claim 1, wherein the resultant adhesive system does not show a significant reduction in bond strength when exposed to an aqueous solution.

3. The dental adhesive system of claim 1, wherein the resultant adhesive system does not show a significant reduction in bond strength when exposed to an aqueous solution for more than one month.

4. The dental adhesive system of claim 1, wherein the resultant adhesive system does not show a significant reduction in bond strength when exposed to an aqueous solution for more than twenty-four months.

5. The dental adhesive system of claim 1, wherein the resultant adhesive system does not show a significant reduction in bond strength when exposed to an aqueous solution for forty-five months or less.

6. The dental adhesive system of claim 1, further comprising a resin operable to be placed over a cured or partially cured mixture of the first portion and the second portion, and wherein the resin is without a hydrophilic monomer.

7. The dental adhesive system of claim 6, wherein the hydrophilic monomer is 2-hydroxyethyl methacrylate (HEMA).

8. The dental adhesive system of claim 1, wherein the multifunctional cross-linking agent is a polymerizable monomer having four or more (meth)acrylate groups.

9. The dental adhesive system of claim 8, wherein the multifunctional polymerizable monomer is selected from the group comprising pentaacrylate and hexacrylate.

10. A dental adhesive system showing improved stability and durability to hydrolytic degradation of bonds, the adhesive system comprising:
  a. a primer adhesive portion formed by the mixture of a part A comprising ethanol and N(p-tolyl) glycine glycidyl methacrylate magnesium salt with a part B comprising a hydrophilic resin comprising biphenyl dimethacrylate (BPDM), 2-hydroxyethyl-methacrylate (HEMA), Bis-phenol glycidylmethacrylate (BisGMA), dipentaerythritol pentaacrylate (DPEPA), and a light cure initiator system; and
  b. a hydrophobic resin;
wherein the dental adhesive system is operable to polymerize to form a dental primer surface.

11. The dental adhesive system of claim 10, wherein the hydrophobic resin further comprises a filler.

12. The dental adhesive system of claim 11, wherein the filler comprises approximately 10%-50% by weight of the adhesive system.

13. A dental adhesive system showing improved stability and durability to hydrolytic degradation of bonds, the adhesive system comprising:
  a. a primer adhesive portion formed by the mixture of a part A comprising ethanol and N(p-tolyl) glycine glycidyl methacrylate magnesium salt with a part B comprising a hydrophilic resin comprising biphenyl dimethacrylate (BPDM), 2-hydroxyethyl-methacrylate (HEMA), Bis-phenol glycidylmethacrylate (BisGMA), dipentaerythritol pentaacrylate (DPEPA), and a light cure initiator system; wherein part B comprises approximately 10% BPDM, about 38.75% HEMA, about 41% BisGMA, about 0.25% camphorquinone (CQ), and about 10% dipentaerythritol pentaacrylate; and
  b. a hydrophobic resin.

14. A dental adhesive system showing improved stability and durability to hydrolytic degradation of bonds, the adhesive system comprising:
  a. a primer adhesive portion formed by the mixture of a part A comprising approximately 25% BisGMA, approximately 25% urethane dimethacrylate (UDMA), approximately 47.77% triethyleneglycol dimethacrylate (Tri-EDMA), approximately 1.75% ethyl 4-dimethylaminobenzoate (EDMAB), approximately 0.45% camphorquinone (CQ), and approximately 0.001% 4-methoxyphenol (MEHQ); with a part B comprising approximately 10% BPDM, about 38.75% HEMA, about 41% bisGMA, about 0.25% camphorquinone (CQ), and about 10% dipentaerythritol pentaacrylate; and
  b. a hydrophobic resin.

* * * * *